United States Patent [19]

Burns

[11] 4,173,977
[45] Nov. 13, 1979

[54] AEROSOL INTERFACE

[75] Inventor: Henry L. Burns, Beaverton, Oreg.

[73] Assignee: Cavitron Corporation, New York, N.Y.

[21] Appl. No.: 781,259

[22] Filed: Mar. 25, 1977

[51] Int. Cl.² ........................................... A61M 15/00
[52] U.S. Cl. .................................... 128/201; 128/186
[58] Field of Search .............. 128/201, 186, 188, 202, 128/203, 192, 193, 194, 195, 196, 197, 205, 208, 209, 210, 145.7, DIG. 2, 173.1, 173.2, 266, 368; 222/193; 137/841, 102, DIG. 9, 803; 261/DIG. 65, DIG. 48

[56] References Cited

U.S. PATENT DOCUMENTS

| 988,352 | 4/1911 | Kerr | 128/186 |
| 2,432,946 | 12/1947 | Theunissen | 128/186 |
| 2,677,370 | 5/1954 | Newton et al. | 128/195 |
| 3,850,171 | 11/1974 | Ball et al. | 128/203 |

FOREIGN PATENT DOCUMENTS 1103522  3/1961  Fed. Rep. of Germany .... 128/DIG. 2

Primary Examiner—Henry J. Recla
Attorney, Agent, or Firm—Brumbaugh, Graves, Donohue & Raymond

[57] ABSTRACT

An aerosol interface comprises a housing defining a fluid receiving chamber in open communication with the atmosphere, with inlet means operatively associated with the housing for permitting continuous delivery to the chamber of a flow of an aerosol fluid so as to obtain an accumulation of the aerosol fluid therein for inhalation by a patient using the aerosol interface. Breath transmission means, operatively associated with the housing, has a passageway therethrough defined by an inner end and an outer end, the outer end being adapted for communication with the breath of a patient using the aerosol interface for the inhalation through the passageway of the aerosol fluid in the chamber and the exhalation of expired fluid by the patient into the passageway. Outlet means is operatively associated with the housing in open communication with the chamber through a channel so as to permit a flow of the expired fluid from the patient to exhaust to the atmosphere, and flow control means are incorporated in the chamber intermediate the transmission means and the outlet means so as to cause substantially all of the expired fluid during exhalation to flow to the atmosphere through the channel of the outlet means without flowing into the chamber.

43 Claims, 14 Drawing Figures

MID-EXHALATION

FIG. 10

END OF EXHALATION
(PRIOR TO INHALATION)

AEROSOL INTERFACE

BACKGROUND OF THE INVENTION

The present invention relates to an aerosol interface device that is particularly suited for therapy applications in which an aerosol fluid is inspired by the patient during each inhalation period.

One of the therapeutic modes of treatment for respiratory diseases is the administration of moisture and/or drugs via an aerosol. Several systems for generating aerosols suitable for respiratory therapy are available commercially. The interface between an aerosol generator and the patient involves several unique problems which are not wholly answered by currently available equipment. The subject invention discloses a new and efficient interface for use in the administration of aerosol therapy.

The basic problem confronting the aerosol generator-patient interface centers on the fact that the breathing patient is a cyclic (inhale-exhale) system while the generator functions best as a continuous flow system. The standard mist tent encloses the patient's head and upper body with an aerosol filled canopy to insure that a supply of concentrated aerosol is readily available for each inhalation cycle, but aerosol fallout over large areas plus excess aerosol output required to preclude carbon dioxide buildup within the enclosure results in aerosol waste and excess aerosol generating capacity requirements. The standard aerosol face tent (a large open top face mask) fails to economize aerosol because the flow of exhaled gases tends to sweep aerosol from the face tent to nullify any pre-inhalation accumulation.

The standard enclosed aerosol mask and the standard mouthpiece have the same problems as the face tent. If a high level of aerosol density is desired all of the standard interface systems require excessively high output flow from the aerosol generator in order to provide undiluted aerosol during peak inspiratory flow rates; the net result is a high level of aerosol waste during exhalation and during low inhale flow rates.

Some aerosol therapy systems attempt to get around the above problems by generating aerosol during inhalation only, but this presents a problem of coordination with the breathing cycle plus loss of effectiveness because most aerosol generators have a significant time lag between start of generation and arrival of aerosol at the patient. The standard aerosol interface systems are not satisfactory because they waste aerosol which may contain a very expensive drug, they require high generating capacity to achieve a desirable inhaled aerosol density, and they are uncontrolled in their rate of delivery to the patient's lung (a fact that can have serious consequences when potent drugs are involved).

An interface system which contains a volume to accumulate aerosol generated during exhalation and provides a double check valve arrangement to steer exhaled gases away from the accumulated aerosol and to direct inhaled gases toward the patient from the accumulator volume and source of aerosol generation, would seem to solve most of the above interface problems. Up until now the typical breathing flow steering valve designs involve a mechanical poppet and valve seat arrangement. Such valves are not satisfactory for aerosol flow control because of an inherent tendency for the movable valve to provide a small flow passage at low flow rates which becomes a means for elimination of the aerosol by coalescence while flowing through the small opening.

The advantages and distinctions of my invention over the prior art will become more clearly evident as the disclosure proceeds, and is obtained by utilizing an accumulator/airflow steering interface system which contains always open, nonrestrictive passageways.

OBJECTS OF THE INVENTION

An object of the present invention is to provide an aerosol interface that is capable of delivering aerosol fluid for respiratory therapy to a patient, and permitting the exiting of expired fluid directly to the atmosphere without mixing with the accumulated aerosol fluid within the aerosol interface.

Another object of the present invention is to provide an aerosol interface, having no moving parts, that automatically permits the flow of aerosol fluid to the patient coinciding with the patient's inhalation, and the exiting of expired fluid from the aerosol interface coinciding with the patient's exhalation, and concurrently maintaining the aerosol and expired fluids free from admixture with each other.

Another object of the present invention is to provide an aerosol delivery system in which the tidal volume of inspired gas is an aerosol that is continuously supplied and stored within the aerosol interface, and the expired tidal volume bypasses the stored supply of aerosol fluid contained within the aerosol delivery system.

Another object of the present invention is to provide a control of the expired flow in an interface device such that, without moving parts, fluid separation is maintained between respective fluids which flow in substantially different directions within the interface device.

Other objects and advantages will become apparent as the disclosure proceeds.

SUMMARY OF THE INVENTION

The outstanding and unexpected results obtained by the practice of the apparatus of this invention are obtained by a series of features and elements assembled and working together in interrelated combination. The aerosol interface comprises a housing having oppositely disposed upper and lower ends with a fluid receiving chamber therein capable of maintaining a supply of an aerosol fluid therein. One such housing is fabricated having a front wall and a rear wall extending between the respective ends, with a pair of oppositely disposed side walls extending intermediate the front and rear walls. An opening, preferably at the lower end of the housing, maintains the chamber in open communication to the atmosphere at the lower end thereof.

Inlet means is provided and operatively associated with one of the walls of the housing for permitting a continuous delivery to the chamber of a flow of aerosol fluid so as to obtain an accumulation of the aerosol fluid therein for inhalation by a patient using the aerosol interface. Aerosol generating means may be removably secured to the inlet means for continuously supplying the desired aerosol fluid to the chamber.

Breath transmission means is operatively associated with the housing, and is preferably in the form of a mouthpiece having a passageway therethrough. The passageway is defined by an inner opening at one end thereof and an outer opening at the other end thereof, with upper and lower surfaces extending intermediate the ends and a pair of oppositely disposed side surfaces intermediate the upper and lower surfaces.

The outer end of the transmission means is adapted for communication with the breath of a patient using the aerosol interface by placement between the patient's lips for the inhalation through the passageway of the aerosol fluid in the chamber and the exhalation of expired fluid by the patient into the passageway. The inner end is in communication with the chamber and preferably is above the inlet means.

To exhaust the expired fluid to the atmosphere during each exhalation period, outlet means is provided in open communication with the atmosphere. The outlet means comprises a channel providing a flow path for the expired fluid from the patient to exhaust to the atmosphere. The channel of the outlet means preferably comprises an upper wall and a lower wall in spaced relationship to each other and a pair of oppositely disposed side walls extending intermediate the upper and lower walls. The lower wall has a terminal end within the chamber, and the spacing between the upper wall and the lower wall at the terminal end defines a channel opening to receive the expired fluid breath from the transmission means. The upper and lower walls diverge gradually from the therefore flow-restricting channel opening to terminate in an exhaust opening to ambient atmosphere. The lower wall extends transversely across the chamber at one end thereof but is spaced from the terminal end and the inner opening of the passageway so as to provide a flow path for the aerosol fluid to the passageway from the chamber during each inhalation period.

Flow control means at one end of the chamber intermediate the transmission means and the outlet means is provided so as to cause substantially all of the expired fluid during exhalation from the passageway to flow to the atmosphere through the channel of the outlet means without flowing into the chamber.

The control means comprises a fluid stream attachment surface configuration merging with the upper surface at one end thereof and the upper wall at the other end thereof. The fluid stream attachment surface tends to direct expired fluid breath flowing from the passageway inner opening through the chamber toward the channel along the fluid stream attachment surface so as to be conducive to a wall-hugging effect in the expired fluid as it passes over or through the chamber and into the channel.

Accordingly, the control means directs substantially all of the expired fluid from the passageway inner opening to flow to the atmosphere through the channel of the outlet means without flowing into the chamber or forcing more than a minimal amount of the aerosol fluid contained in the chamber out through the outlet means during each patient exhalation period. In this manner the aerosol fluid in the chamber remains substantially free of the expired fluid such that the fluid inspired by the patient during each inhalation period is primarily aerosol fluid from the chamber.

The configuration of the fluid control means and the positionment of the outlet means may vary in accordance with the preferred embodiments of the invention as desired therein. For example, in accordance with one embodiment of the invention, the fluid stream attachment surface configuration comprises a first deflecting curved surface which is concave in a plane transverse to the flow from the inner opening and merges, at one end thereof, with the upper surface of the passageway and a second curved deflecting surface which is convex in a plane transverse to the flow from the inner opening and merges with the first deflecting surface at one end thereof and the upper wall.

In accordance with another embodiment of the invention, the contoured fluid stream attachment surface configuration comprises a first deflecting surface extending substantially in a vertical plane transverse to the flow from the inner opening and merging with the upper surface at one end thereof, and a second deflecting surface extending substantially in a horizontal plane transverse to the flow from the inner opening and merging with the first deflecting surface at one end thereof and with the upper wall at the other end thereof.

A further embodiment of the invention provides a channel opening that extends below the elevation of the passageway inner opening with the control means extending therebetween, and in which the lower wall extends in substantially a vertical plane and the upper wall is outwardly inclined relative to the lower wall, with the contoured fluid stream attachment surface forming an arc extending in a plane transverse to the flow from the inner opening and merging with the upper surface at one end thereof and the upper wall at the opposite end thereof.

Accordingly, the present invention, in each of its embodiments, provides for an efficient and simplified manner of essentially maintaining two separate fluids apart from each other without any type of valve arrangement. The novle structure of the present invention permits a direct flow path for the expired fluid, and a separate flow path for the inspired aerosol fluid. The control means provides the necessary direction to the expired fluid such that it bypasses the chamber of the aerosol interface, while aerosol fluid is continuously provided therein. The term "aerosol" as used herein is not intended to be limited as to any particle size of the fluid droplets that are formed.

Reference to upper versus lower position or end of the interface is made for descriptive convenience only. The interface may be held horizontally or upside down with respect to gravity with minimum influence on overall performance.

BRIEF DESCRIPTION OF THE DRAWINGS

Although the characteristic features of this invention will be particularly pointed out in the claims, the invention itself, and the manner in which it may be made and used, may be better understood by referring to the following description taken in connection with the accompanying drawings forming a part hereof, wherein like reference numerals refer to like parts throughout the several views and in which:

DESCRIPTION OF PREFERRED EMBODIMENTS

Referring to the drawings, there is illustrated in FIGS. 1 through 12 an aerosol interface 10 adapted to be used by a patient 12 for inhalation of an aerosol fluid and subsequent exhalation of an expired fluid on a periodic basis. The aerosol interface 10 includes a housing 14 that is of a size that is readily adapted to be hand held by the user 12 in a manner illustrated in FIG. 1.

Figures 2, 3, 4:
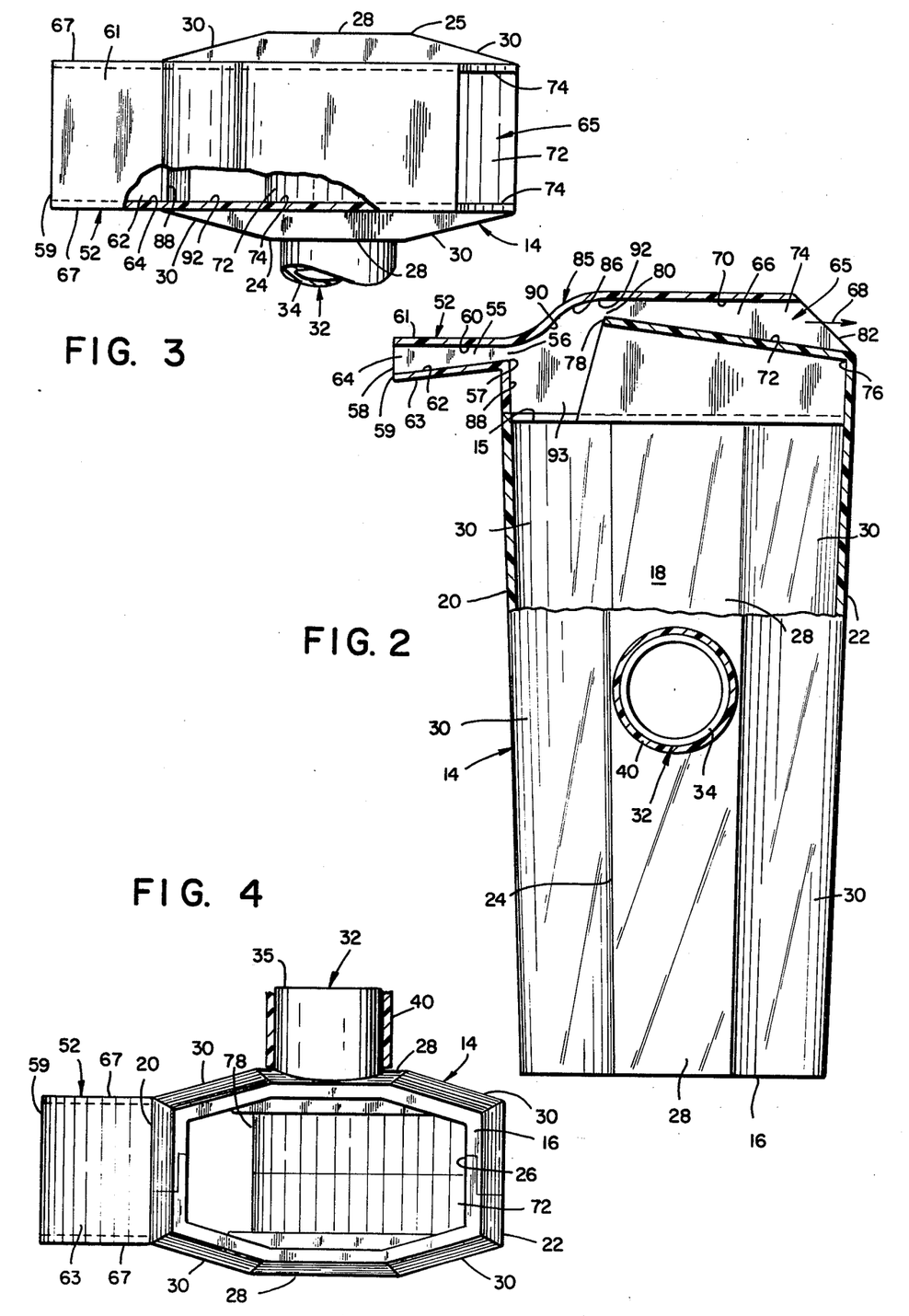
FIG. 2 is a side plan view, partly in section, of the aerosol interface.
FIG. 3 is a top plan view of the aerosol interface of FIG. 1, partly in section.
FIG. 4 is a bottom plan view of the aerosol interface illustrated in FIG. 2.

The housing 14, which may be fabricated from a plastic material in one or more sections, is assembled having the configuration illustrated in FIGS. 2, 3 and 4. The housing 14, which may vary in both shape and size, includes an oppositely disposed upper end 15, lower end 16, with a fluid receiving chamber 18 therein. The housing 14 further includes a front wall 20 which forms the front side of the housing 14 and a rear wall 22 which forms the rear side of the housing 14. A pair of oppositely disposed side walls 24 and 25 extend intermediate the front wall 20 and rear wall 22. An opening 26 is provided at the lower end 16 of the housing 14 so as to maintain the chamber 18 in open communication to the atmosphere.

The side walls 24 and 25 may be formed having a vertically extending central section 28 and an inwardly inclined side section 30 that merges with the front wall 20 and rear wall 22. The chamber or cavity 18 has a volume of approximately 400 ml for use by an adult patient.

Figure 1:
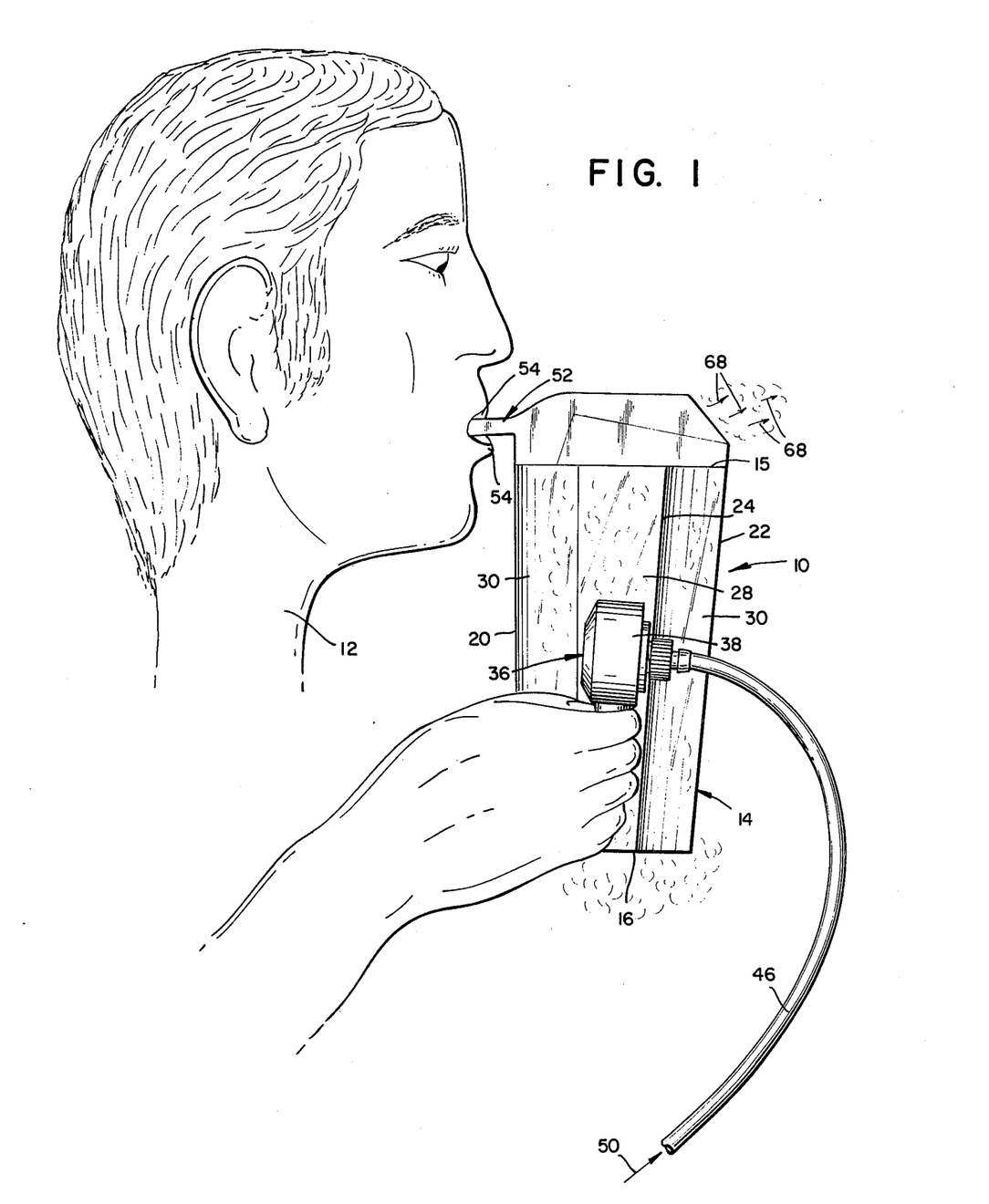
FIG. 1 is a side plan view of the aerosol interface in accordance with the present invention as utilized by a user thereof.

To provide a continuous supply of aerosol fluid to the chamber 18, there is provided inlet or inflow means 32 operatively associated with the housing 14. The inlet means 32 may be in the form of a tubular element or member 34 that extends outwardly from one of the side walls. As illustrated in FIGS. 2-4, the tubular element 34 extends outwardly from side wall 24 having an input end 35 adapted to be connected to aerosol generating means 36, as illustrated in FIG. 1.

Figure 5:
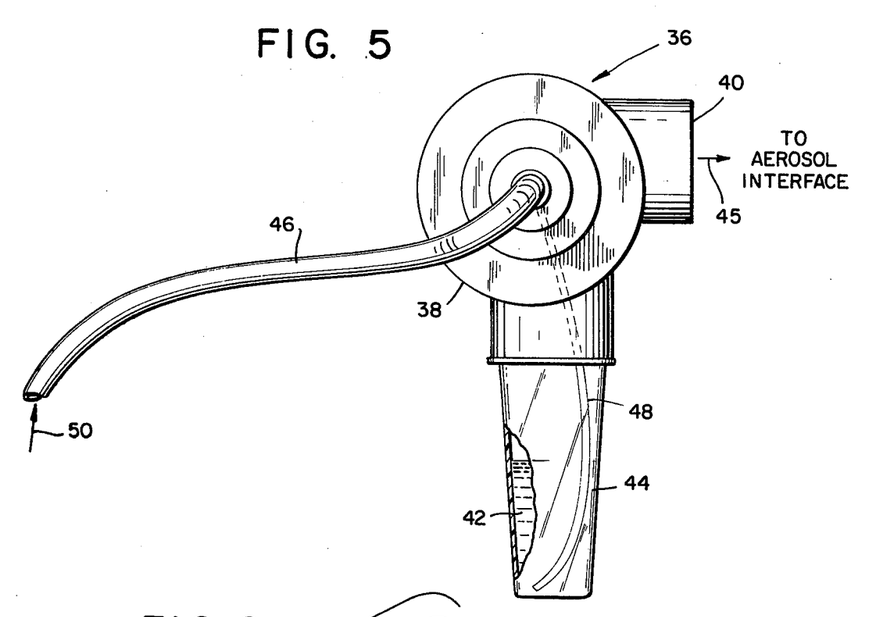
FIG. 5 is a side plan view of a typical aerosol generating assembly adapted for use with the aerosol interface of the present invention.
Figure 6:
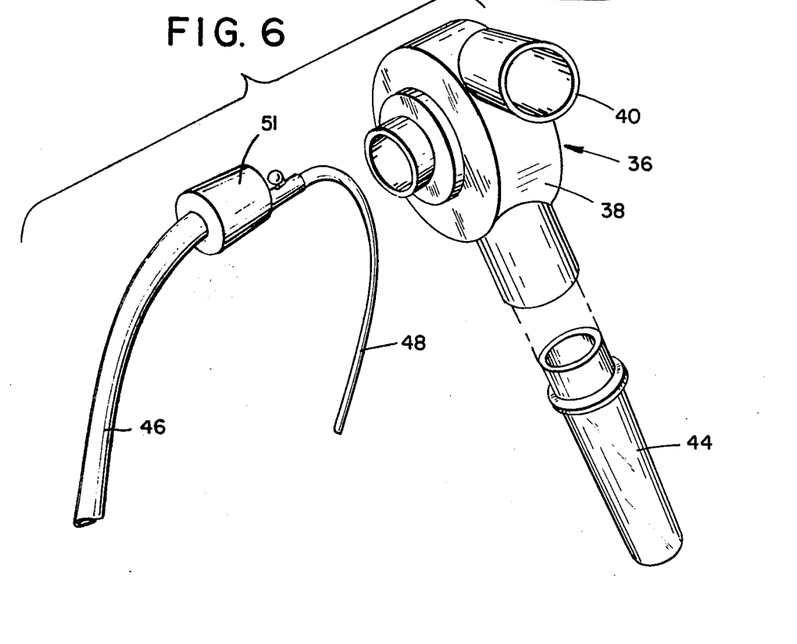
FIG. 6 is a perspective view, in exploded relationship, of the parts comprising the typical aerosol generating assembly.
Figure 7:
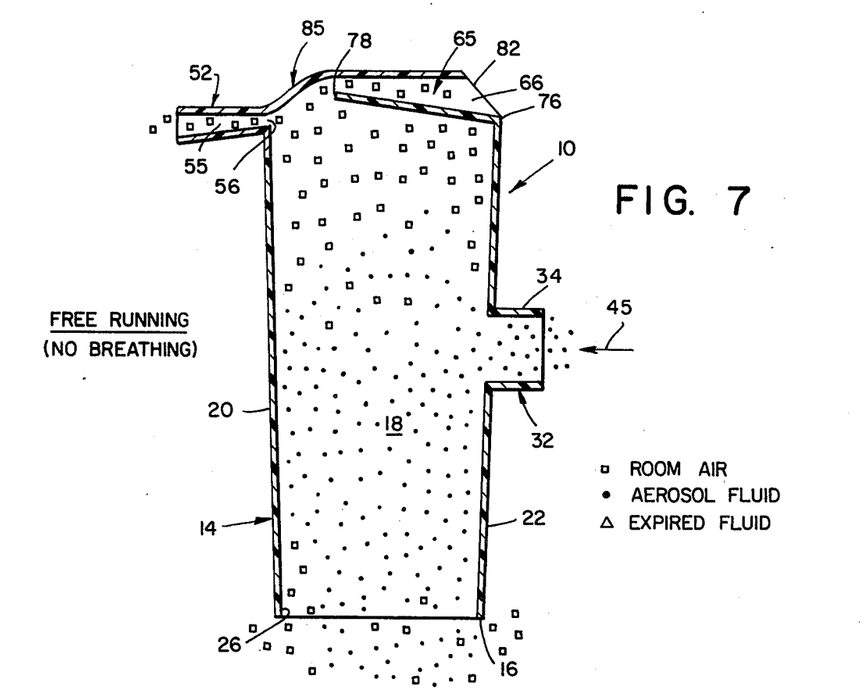
FIGS. 7 through 10 are diagrammatic views to illustrate the workings of the present invention.

The aerosol generating means 36, as illustrated in FIGS. 5 and 6, may take various forms and shapes, and be of a construction well known in the art. The aerosol generating means 36 includes a housing 38 having a coupling conduit 40 adapted to extend in telescopic relationship with the tubular element 34.

The aerosol generating means 36 includes a removable atomizing module 51 adapted for insertion into housing 38 with an integral uptake tube 48 extendable into a removable reservoir 44 containing fluid 42 that is to be continuously formed into an aerosol fog or fluid that is transmitted in the direction of arrow 45 to chamber 18. A compressed gas input flow line 46 transmits gas in the direction of arrow 50 from a suitable source under pressure to and through atomizing module 51 to provide the energy for fluid uptake and atomization and becomes a component of the aerosol fluid leaving the aerosol generating means 36 via conduit 40.

The input gas may be selected by the physician depending upon the needs of the patient. In a similar manner the liquid 42 may also vary for the particular medical condition of the patient 12 utilizing the aerosol interface 10. The particular aerosol generating means 36 and atomizing module 51 to supply a continuous duty function of fluid to the aerosol interface may be of the type disclosed in U.S. Pat. No. 3,744,722.

The aerosol generating means 36 is designed to continuously supply aerosol fluid to the chamber 18. In contrast, the breathing by the patient 12 is a cyclic function, and therefore we have the problem of a continuous supply of aerosol fluid and only an intermittent or periodic intake of the aerosol fluid by the patient 12. The present invention is so designed as to permit in effect an accumulation or storage of the atomized fluid in the chamber 18, and a withdrawal of the atomized fluid coinciding with the inhalation period of the user 12. The aerosol interface also permits the expired or exhaled fluid on each exhalation by the patient to exit from the aerosol interface 10 in a manner to substantially bypass the chamber 18.

To permit the free breathing of the patient, there is provided breath transmission means or mouthpiece 52, which is dimensioned to be readily positioned between the lips 54 of the user in order to readily engage same. The breath transmission means 52 is operatively associated with the housing 14 and is provided with a passageway 55 therethrough. Passageway 55 is defined by an inner opening 56 at one end 57 thereof and an outer opening 58 at the other end 59 thereof. The exact shape of the passageway 55 is defined by an upper surface 60, forming part of the top wall 61, and lower surface 62, forming part of the bottom wall 63. The surfaces 60 and 62 are inclined relative to each other and taper outwardly from the inner opening 56 to the outer opening 58. End surfaces 64 extend intermediate the upper and lower surfaces 60 and 62, respectively, and are formed on end walls 67.

The outer end 58 of the transmission means 52 is adapted for communication with the breath of the patient 12 using the aerosol interface 10 for the inhalation through the passageway 55 of the aerosol fluid in the chamber 18 and the exhalation of expired fluid by the patient into the passageway 55. The inner end 56 is in communication with the chamber 18 and extends above the inlet means 32.

To provide the necessary exiting from the aerosol interface 10 of the expired fluid, there is provided outlet means 65 operatively associated with the housing 14 at substantially one end thereof. The outlet means 65 comprises a channel 66 to permit a flow path in the direction of single headed arrow 68 of the fluid that exits from the outlet means 65. The fluid indicated by the arrows 68 in FIG. 1 is primarily the expired fluid from the patient 12. The process of the inhalation and exhalation will hereinafter be more fully discussed with respect to FIGS. 7 through 10.

The channel 66 defines the flow path for the exhaled fluid in the direction of arrow 68 to exhaust to the atmosphere. As is evident from FIG. 2, the transmission means 52 and outlet means 65 are in substantial alignment with each other to provide a direct flow path for the expired fluid. The channel 66 includes an upper wall 70 and a lower wall 72 in spaced relation thereto with oppositely disposed side walls 74 extending intermediate the upper wall 70 and lower wall 72. The lower wall 72 forms in effect a partition extending transversely across the width of the chamber 18 and merging at its back end 76 with the rear wall 22.

The lower wall 72 has a terminal end 78 in spaced relationship to the back end 76. The spacing between the upper wall 70 and the lower wall 72 at the terminal end 78 defines a channel opening 80 to receive the expired fluid breath from the transmission means 52. As illustrated in FIG. 2, the upper and lower walls 70 and 72, respectively, diverge gradually outwardly from each other to terminate in an exhaust or fluid opening 82.

To permit the sequential operation, there is provided flow control means 85 which extends at one end of chamber 18 intermediate the transmission means 52 and the outlet means 65 so as to cause substantially all of the expired fluid during exhalation from the passageway 55 to flow to the atmosphere through channel 66, without flowing into the chamber 18. By accomplishing this, the expired fluid does not mix with the aerosol fluid which is to be inspired by the patient upon each inhalation. Accordingly, the control means 85 directs the expired fluid such that it exits through the exhaust opening 82 to the ambient atmosphere and the chamber remains free of expired fluid.

The control means 85 comprises a fluid stream attachment surface 86 merging with the upper surface 60 at one end thereof and the upper wall 70 at the other end thereof. The fluid stream attachment surface 86 tends to direct exhaled fluid breath flowing from the passageway inner opening 56 above the chamber 18 toward the channel 66 along the fluid stream attachment surface 86 so as to be conducive to a wall-hugging effect in the exhaled fluid as it passes above the chamber 18 and into the channel 66 through the channel opening 80. The particular wall-hugging or flow biasing effect described herein is disclosed more fully in U.S. Pat. No. 3,472,225, and the subject matter thereof is incorporated herein by reference.

To obtain the desired flow from the passageway 55, two distinct patterns are developed, one being along the fluid stream attachment surface 86 that merges with the upper surface 60 and upper wall 70, and the other in the form of a breakaway surface 88 that merges with the lower surface 62 of passageway 55. The breakaway surface 88 may be in alignment with the front wall 20 of the housing 14. The transmission means 52, outlet means 65, and control means 85, may be formed on a separate assembly adapted to snap onto, or otherwise connected, to the upper end 15 of the housing 14. This permits ready disassembly for cleaning of the aerosol interface 10.

The fluid stream attachment surface 86 in accordance with the embodiment of the invention presently being described, includes a first deflecting surface 90 that is concave in a plane transverse to the flow from the inner opening 56 and merging with the upper surface 60 at one end thereof. A second deflecting surface 92 is convex in configuration and extends in a plane transverse to the flow from the inner opening 56. The convex deflecting surface 92 merges with the first deflecting surface 90 at one end thereof and with the upper wall 70 at the other end thereof. The upper wall 70 may in effect define the upper end of the aerosol interface 10.

The channel opening 80 extends above the elevation of the passageway inner opening 56 such that the control means 85 directs the expired fluid upwardly therealong as an airstream which hugs the fluid stream attachment surface. The lateral spacing between the end surfaces 64 and side walls 74 may be of equal dimension and having coupling side surfaces 93 extending therebetween.

The aerosol interface 10 may readily be held by the user 12, or if desired may be supported on a support surface while the user 12 is seated or in a bed. The construction is such that the channel 66 is characterized in that the upper wall 70 and lower wall 72 diverge to provide a cross-sectional area increasing in the flow direction from the channel opening 80 to the atmosphere. There are no mechanical valves that are required for the operation of the aerosol interface 10.

To help describe the process of the present invention, FIGS. 7 through 10 have been provided to illustrate in a diagrammatic manner the distribution of the various fluids or gases within the chamber 18 during the utilization of the aerosol interface 10. Commencing with FIG. 7, there is illustrated the aerosol interface 10 in a free running condition in which there is no breathing taking place by the user. As illustrated in chamber 18, there is contained room air which is symbolically shown, and aerosol fluid entering the chamber 18 in the direction of arrow 45. For purposes of illustration, the inlet means 32 is situated on the rear wall 22 of the housing 14. As illustrated, the aerosol fluid tends to spill out from the lower end 16 through the opening 26. The reason for this is that the aerosol, due to its weight and coldness, will drift downwardly and out from the opening 26 which is connected to ambient.

Figure 8:
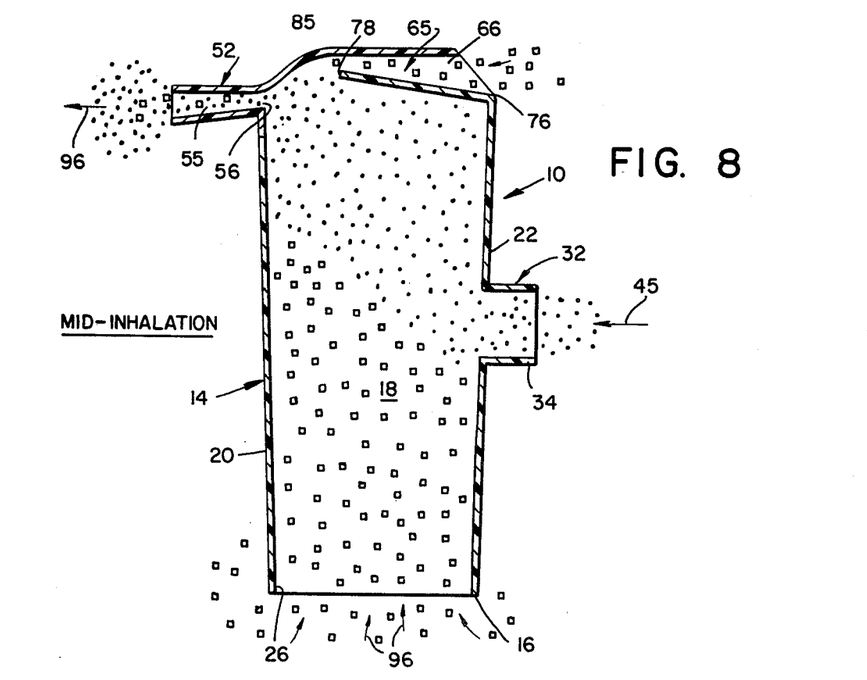

FIG. 8 illustrates the condition of the aerosol interface 10 during the mid-inhalation of the user 12. As can be seen the aerosol fluid illustrated therein tends to move directly to the transmission means 52 since an inhaling force is provided by the user.

As will be seen in FIG. 8, very little room air is inspired by the patient at the mid-inhalation period. A certain amount of room air is situated within the channel 66 of the outlet means 65. In addition, room air is situated at the lower end of the chamber 18 below the aerosol fluid. In this manner the patient during the inhalation period or cycle breathes in substantially only aerosol fluid.

Figure 9:
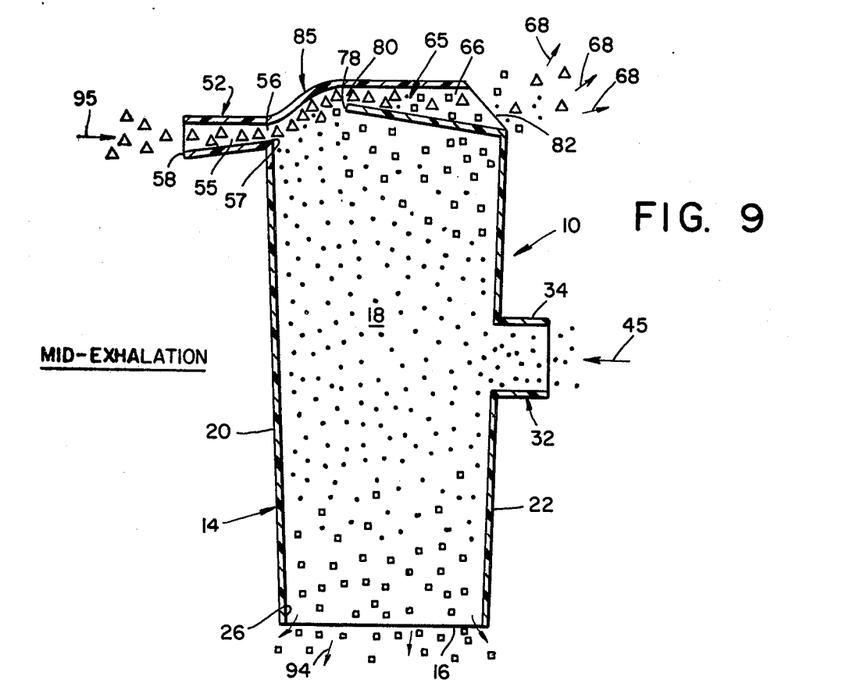

Referring now to FIG. 9, there is represented the mid-exhalation period, during which time the patient is exhaling expired fluid or gases which is symbolically illustrated. It is during this period of time that the expired fluid is desired to be removed from the aerosol interface 10 without drifting into or otherwise accumulating within the chamber 18. It must be appreciated that the aerosol generating means is continuously supplying to the chamber aerosol fluid. This aerosol fluid is accumulating and is ready for inhalation when the patient next inspires.

As illustrated in FIG. 9, during the mid-exhalation period expired gas flows outwardly through the channel 66 as illustrated by arrows 68. In addition, certain room air may also be aspirated out through the channel 66. A certain amount of room air within the lower end of the chamber 18 may also be aspirated or displaced out from the bottom end 16 in the direction of arrows 94. In this manner due to the novel construction of the coupling means 85, substantially all of the expired fluid flows outwardly through the channel opening 80 to the atmosphere.

Figure 10:
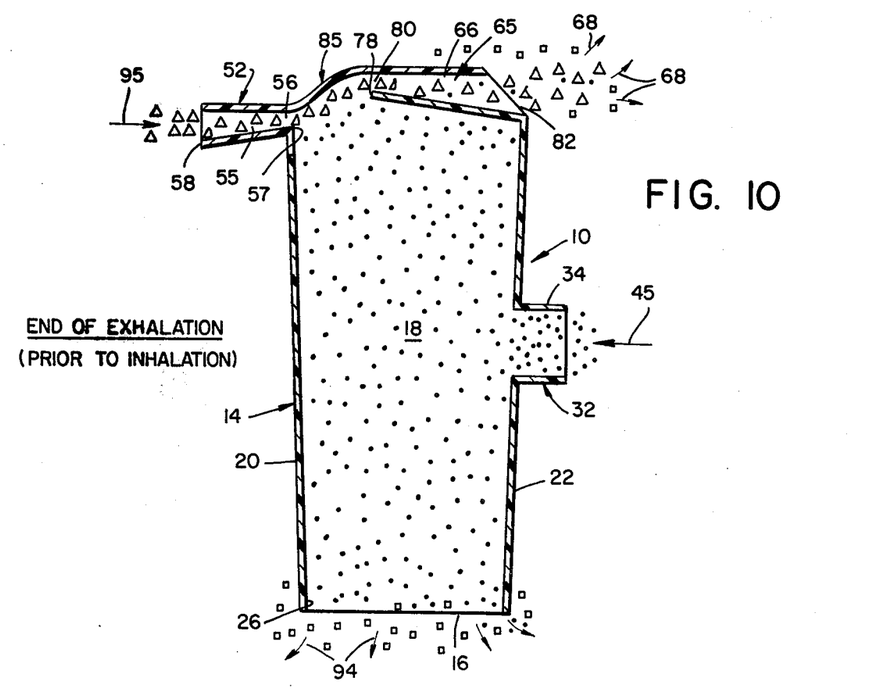

FIG. 10 illustrates the exhalation period at the end thereof, and just prior to the start of the next succeeding inhalation period by the user of the device. As illustrated in FIG. 10, the exhaled or expired fluid is entering the transmission means 52 in the direction of arrow 95, and due to the velocity thereof by the patient, and the interrelated combination of the transmission means 52, flow control means 85, and outlet means 65, substantially all of the expired fluid exits from the aerosol interface through the fluid opening 82. By accomplishing this procedure, the chamber 18 remains free of expired fluid since substantially all of it has exited in the direction of arrows 68.

Also during the exhalation period the continuous inflow of aerosol through inlet 34, plus aspiration of trapped room air into passage 65 to exit from opening 82, plus downward displacement of room air from chamber 18 opening 16, has resulted in chamber 18 being completely filled with aerosol fluid only in readiness for the forthcoming inhalation.

The theroretical considerations to obtain this phenomenon are related to the geometrical configuration of the surfaces previously described with respect to FIGS. 2-4 and the dimensional relationship as hereinafter described with respect to FIGS. 11 and 12. Upon the completion of an exhalation cycle by the patient, the patient would then inspire aerosol fluid in the manner illustrated with respect to FIG. 8. This process, unbeknownst to the patient, reoccurs automatically as the aerosol interface 10 is continuously utilized. In this manner upon each inhaling breath aerosol fluid in the direction of arrow 96 is inhaled by the patient.

It must be appreciated that the ability to maintain the aerosol fluid searate from the expired fluid also produces an economical saving as well as a health saving to the patient. By using the aerosol interface of the present invention, aerosol generating means may be utilized that is continuously delivering aerosol fluid to the chamber, even though it is intermittently removed therefrom for use by the patient.

Figures 11, 12:
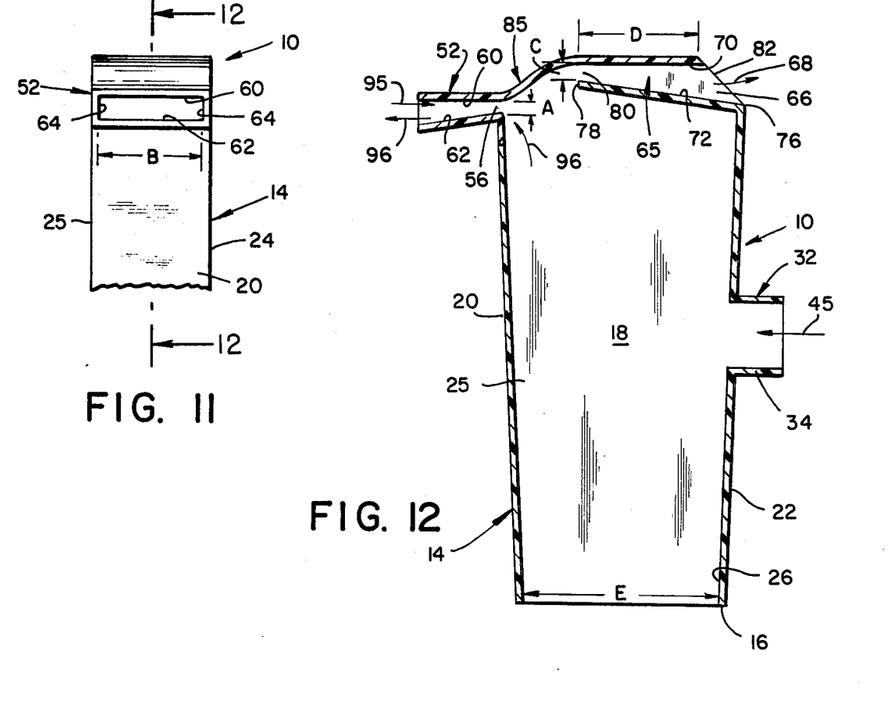
FIG. 11 is a fragmentary front plan view of the aerosol interface to illustrate the dimensions thereof.
FIG. 12 is a sectional view taken along lines 12—12 of FIG. 11.

Referring now to FIGS. 11 and 12, there is illustrated the preferred dimensional relationship between the various portions of the aerosol interface 10 in order to obtain the desired flow characteristics therethrough. The dimensions are described as a multiple of dimension A, which is defined as a vertical spacing between the upper surface 60 and the lower surface 62 at the passageway inner opening 56.

For an adult chamber having a volume of between 400 to 500 ml, it has been found that dimension A is approximately 0.100 inch in height. In conjunction with dimension A the width of the transmission means 52, dimension B as defined by the spacing between the end surfaces 64, is defined at approximately twelve times greater than dimension A. Dimension C defines the size of the throat of channel opening 80. The dimension C is measured between the terminal end 78 of the lower wall 72 and the upper wall 70 extending thereabove. Dimension C is approximately two times as large as that of dimension A.

The length of the channel 66 is indicated by dimension D, which starts at the terminal end 78 and may extend rearwardly to the exhaust opening 82. Dimension D is approximately ten times greater than dimension A. The exhaust opening 82 may be inclined at approximately 45° to the upper wall 70.

The opening 26 at the lower end 16 of the housing 14 is defined by dimension E. It has been found that dimension E is to be in the range of fifteen to twenty-five times as large as dimension C. These relations between sectional opening dimensions A, C and E are dependent on width dimension B remaining substantially constant.

The above described dimensional relationship has been found ideally suited for an aerosol delivery system, but the invention is not limited to these specific dimensions, and it is believed that alterations of these dimensions by as much as 25 percent will not seriously affect the performance of the aerosol delivery features of the present invention. The ability to in effect isolate the aerosol fluid from the expired fluid is most important since the aerosol fluid which is being produced may be costly and any savings thereof is most important. The present invention in a simple and efficient manner, without any moving parts, provides for the selective delivery of the expired fluid to the atmosphere while the aerosol fluid remains ready to be inhaled by the user during inhalation.

The above interrelationship of dimensions is such as to produce the desired flow through the aerosol interface while it is continuously used by the patient for a variety of applications. It is appreciated that the present invention is not necessarily limited to medical applications but may have other uses in industry where it is desired to provide an interface between a continuous duty function where a fluid (gas or liquid) is being transferred across or through an interface.

Accordingly, the transmission means could be coupled to apparatus that requires the supply of a fluid from the chamber during a portion of a given cycle, and during another portion of a given cycle expired fluid exits through the aerosol interface as hereinabove described.

Figure 13:
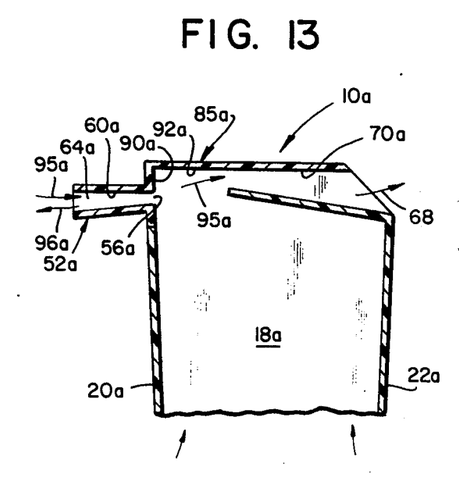
FIGS. 13 and 14 are fragmentary views illustrating alternate embodiments of the invention.

Referring now to FIG. 13, there is illustrated another embodiment of the present invention in which the configuration of the flow control means is different than as previously described. The aerosol interface 10a may be similarly constructed in the manner previously described, except that the flow control means 85a is such that the first deflecting surface 90a extends substantially in a vertical plane transverse to the flow from the inner opening 56a of the passageway 64a of the breath transmission means 52a.

The first deflecting surface 90a merges with the upper surface 60a at substantially right angle thereto. The second deflecting surface 92a extends substantially in a horizontal plane transverse to the flow from the inner opening 56a and merging with the first deflecting surface 90a at one end thereof and with the upper wall 70a at the other end thereof.

The embodiment of FIG. 13 has been found to also provide the necessary flow pattern as indicated at one end by arrow 95a and at the other end by arrow 68a. The flow characteristics of the respective aerosol fluid and expired fluid would act in a similar manner as previously described with respect to FIGS. 7 through 10.

Figure 14:
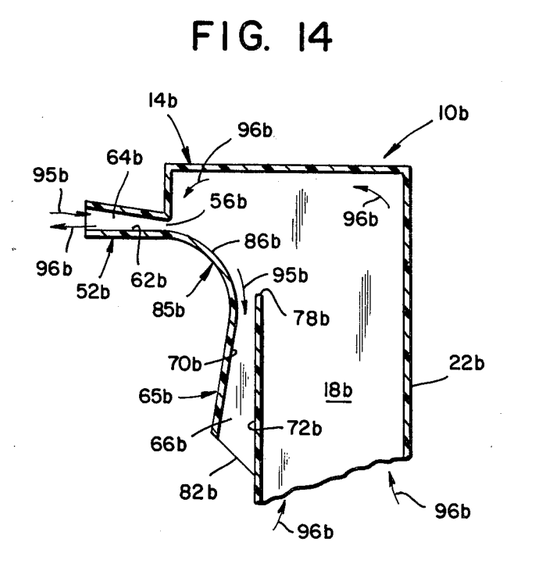

Referring now to FIG. 14, there is illustrated another embodiment of an aerosol interface 10b, in accordance with the present invention. In this embodiment the outlet means 65b is positioned such that the channel 66b extends below the elevation of the passageway 64b. As illustrated, the transmission means 52b extends outwardly from the housing 14b on one side thereof and the coupling means 85b is interposed between the transmission means 52b and the outlet means 65b.

In the embodiment of FIG. 14 the outlet means 65b may be situated on the same side of the housing 14b as is the transmission means 52b. The outlet means 65b includes an upper wall 70b and a lower wall 72b in a similar manner as previously described. The coupling means 85b in this embodiment includes a fluid stream attachment surface 86b that forms an arc merging at one end with the lower surface 62b and at the other end with the upper wall 70b of channel 66b. It has been found that the expired fluid in the direction of arrow 95b is sufficient in that it hugs the fluid stream attachment surface 86b and exits through the channel 66b.

In this manner the embodiment of the invention illustrated in FIG. 14 functions in the manner described with respect to FIGS. 7-10, even though the outlet means 65b is situated below the passageway inner opening 56b. The expired fluid will exit from the fluid opening 82b in the same manner as illustrated in the previous embodiment of the invention.

In operation the mouthpiece is held in the patient's mouth while he inhales and exhales continuously and normally through the mouthpiece. The aerosol generating source provides a continuous flow of gas with its suspended aerosol which enters the interface system through the aerosol inlet means, and a variety of liquids may be used to form the aerosol.

The enclosure housing need not be thin nor rectangular, as shown, as long as the desired volume is enclosed and its height is greater than its maximum cross section dimension.

Although illustrative embodiments of the invention have been described in detail herein with reference to the accompanying drawings, it is to be understood that the invention is not limited to the precise embodiments, and that various changes and modifications may be effected therein without departing from the scope or spirit of the invention.

I claim:
1. An aerosol interface comprising:
   A. a housing defining a fluid receiving chamber having an upper end and a lower end in open communication with the atmosphere,
   B. inlet means disposed on said housing between said upper and lower ends for permitting continuous delivery to said chamber of a flow of aerosol fluid so as to obtain an accumulation of the aerosol fluid therein for inhalation by a patient using the aerosol interface,
   C. breath transmission means operatively associated with said housing and having a passageway therethrough, said passageway being defined by an inner opening at one end thereof in direct continuously open fluidic communication with said chamber and extending above said inlet means, and an outer opening at the other end thereof, with upper and lower surfaces extending intermediate said ends,
   D. said outer opening being adapted for communication with the breath of a patient using the aerosol interface for the inhalation through said passageway of the aerosol fluid in said chamber and the exhalation of expired fluid by the patient into said passageway,
   E. outlet means operatively associated with said housing in open communication with said chamber and with the atmosphere, said outlet means comprising a channel in direct continuously open fluidic communication with said chamber to permit a flow path for the expired fluid from the patient to exhaust to the atmosphere, and
   F. flow control means at the upper end of said chamber for fluidically coupling said transmission means and said outlet means so as to cause substantially all of the expired fluid during exhalation from said passageway inner opening to flow in open communication to the atmosphere through said channel of said outlet means without flowing into said chamber.

2. An aerosol interface as in claim 1, wherein said control means comprises a contoured fluid stream surface tending to direct the expired fluid breath flowing from said passageway inner opening directly toward said channel along said fluid stream surface as so to be conducive to a wall-hugging effect in the expired fluid as it passes through said chamber and into said channel such that it exits to the atmosphere.

3. An aerosol interface as in claim 1, further including aerosol generating means coupled to said inlet means so as to provide a continuous supply of the aerosol fluid to said chamber.

4. An aerosol interface comprising:
   A. a housing defining a fluid receiving chamber having an upper end and a lower end in open communication with the atmosphere,
   B. inlet means disposed on said housing between said upper and lower ends for permitting continuous delivery to said chamber of a flow of aerosol fluid so as to obtain an accumulation of the aerosol fluid therein for inhalation by a patient using the aerosol interface,
   C. breath transmission means operatively associated with said housing and having a passageway therethrough, said passageway being in direct continuously open fluidic communication with said chamber and defined by an inner opening at one end thereof extending above said inlet means, and an outer opening at the other end thereof, with upper and lower surfaces extending intermediate said ends,
   D. said outer opening being adapted for communication with the breath of a patient using the aerosol interface for the inhalation through said passageway of the aerosol fluid in said chamber and the exhalation of expired fluid by the patient into said passageway,
   E. outlet means operatively associated with said housing and disposed above said inlet means, said outlet means being in open communication with said chamber and with the atmosphere and comprising a channel in direct continuously open fluidic communication with said chamber and having an upper wall and a lower wall in spaced relationship to each other and a pair of oppositely disposed side walls extending intermediate said upper and lower walls, said lower wall having a terminal end within said chamber, the spacing between said upper and lower walls at said terminal end defining a channel opening to receive the expired fluid breath from said transmission means, and
   F. flow control means for fluidically coupling said transmission means to said outlet means to provide an unobstructed path therebetween, said flow control means comprising a contoured fluid stream surface interconnected between said upper wall of said channel and said upper surface of said passageway and tending to cause expired fluid breath flowing from said passageway inner opening toward said channel to hug said contoured fluid stream surface as it passes to said channel to exit to the atmosphere without flowing into said chamber.

5. An aerosol interface as in claim 4, wherein said channel opening extends above the elevation of said passageway inner opening with said control means extending therebetween.

6. An aerosol interface as in claim 5, wherein said fluid stream surface configuration comprises:

a. a first deflecting surface concave in a plane transverse to the flow from said inner opening and merging with said upper surface at one end thereof, and b. a second deflecting surface convex in a plane transverse to the flow from said inner opening and merging with said first deflecting surface at one end thereof and with said upper wall at said other end thereof.

7. An aerosol interface as in claim 5, wherein said transmission means and said outlet means are situated on opposite sides of said housing.

8. An aerosol interface as in claim 5, wherein said contoured fluid stream surface configuration comprises:
 a. a first deflecting surface extending substantially in a vertical plane transverse to the flow from said inner opening and merging with said upper surface at one end thereof, and
 b. a second deflecting surface extending substantially in a horizontal plane transverse to the flow from said inner opening and merging with said first deflecting surface at one end thereof and with said upper wall at said other end thereof.

9. An aerosol interface as in claim 4, wherein said channel opening extends below the elevation of said passageway inner opening with said control means extending therebetween.

10. An aerosol interface as in claim 9, wherein
 a. said lower wall extends in substantially a vertical plane and said upper wall is outwardly inclined relative to said lower wall, and
 b. said contoured fluid stream surface is in the form of an arc extending in a plane transverse to the flow from said inner opening and merging with said upper surface at one end thereof and said upper wall at the opposite end thereof.

11. An aerosol interface as in claim 4, wherein said channel is characterized in that said upper wall and said lower wall diverge provide a cross-sectional area increasing in the flow direction from said channel opening to the atmosphere.

12. An aerosol interface as in claim 4, wherein
 a. said inner opening of said passageway defines a spacing extending between said upper surface and said lower surface,
 b. said channel opening defines a spacing extending between said upper wall and said lower wall at said terminal end, and
 c. said spacing of said channel opening being approximately twice the dimension as said spacing of said passageway inner opening.

13. An aerosol interface as in claim 12, wherein
 a. said passageway has a width defined by oppositely disposed end surfaces extending intermediate said upper and lower surfaces, and
 b. said width of said passageway being approximately twelve times greater than the dimension forming the height of said inner opening as defined by said upper and lower surfaces.

14. An aerosol interface as in claim 12, wherein said channel is of a length approximately ten times greater than the dimension defined by said spacing of said passageway inner opening.

15. An aerosol interface as in claim 12, wherein said housing comprises:
 a. an upper end and spaced apart lower end,
 b. a front wall and a spaced apart rear wall extending between said respective ends,
 c. a pair of oppositely disposed side walls extending intermediate said front and rear walls, and
 d. an opening at said lower end of said housing so as to maintain said chamber in open communication to the atmosphere.

16. An aerosol interface as in claim 15, wherein the cross-sectional area formed by the spacing of said opening extending between said front and rear walls is in the range of approximately fifteen to twenty five times the cross-sectional area formed by said spacing of said passageway inner opening.

17. An aerosol interface as in claim 12, wherein the dimension of the spacing between said upper surface and said lower surface at said inner opening is approximately 0.100 inch.

18. An aerosol interface as in claim 17, wherein the spacing between said upper surface and said lower surface at said outer opening is greater than at said inner opening.

19. An aerosol interface as in claim 18, wherein said transmission means at the outer end thereof is adapted to be readily positioned between the lips of the user of the aerosol interface.

20. An aerosol interface comprising:
 A. a housing having oppositely disposed upper and lower ends with a fluid receiving chamber therein, said housing having a front and a rear wall extending between said respective ends, with a pair of oppositely disposed side walls extending intermediate said front and rear walls, and an opening at said lower end of said housing so as to maintain said chamber in open communication to the atmosphere,
 B. inlet means operatively associated with one of said walls of said housing for permitting a continuous delivery to said chamber of a flow of aerosol fluid so as to obtain an accumulation of the fluid therein for inhalation by a patient using the aerosol interface,
 C. breath transmission means operatively associated with said housing and having a passageway therethrough, said passageway being defined by an inner opening at one end thereof and an outer opening at the other end thereof, with upper and lower surfaces extending intermediate said ends and a pair of oppositely disposed end surfaces intermediate said upper and lower surfaces,
 D. said outer end of said transmission means being adapted for communication with the breath of a patient using the aerosol interface for the inhalation through said passageway of the aerosol fluid in said chamber and the exhalation of expired fluid by the patient into said passageway, said inner end being in open communication with said chamber and extending above said inlet means,
 E. outlet means operatively associated with said housing in open communication with said chamber and with the atmosphere, said outlet means providing a channel to permit a flow path for the expired fluid from the patient to exhaust to the atmosphere,
 F. said channel of said outlet means comprising
  (1) an upper wall and a lower wall in spaced relationship to each other and a pair of oppositely disposed side walls extending intermediate said upper and lower walls,
  (2) said lower wall having a terminal end within said chamber, said spacing between said upper wall and said lower wall at said terminal end defining a channel opening to receive the expired fluid breath from said transmission means, said upper and lower walls diverging gradually to terminate in an exhaust opening to ambient atmosphere, G. flow control means being defined at one end of said chamber intermediate said transmission means and said outlet means so as to cause substantially all of the expired fluid during exhalation from said passageway to flow to the atmosphere through said channel of said outlet means without flowing into said chamber, and H. said control means comprising a fluid stream attachment surface configuration merging with said upper surface at one end thereof and said upper wall at said other end thereof, said fluid stream attachment surface tending to direct expired fluid breath flowing from said passageway inner opening through said chamber toward said channel along said fluid stream attachment surface so as to be conducive to a wall-hugging effect in the expired fluid as it passes through said chamber and into said channel.

21. An aerosol interface as in claim 20, wherein said control means includes a breakaway surface merging with said lower surface.

22. An aerosol interface as in claim 20, wherein said channel opening extends above the elevation of said passageway inner opening with said control means extending therebetween.

23. An aerosol interface as in claim 20, wherein said fluid stream attachment surface comprises:
a. a first deflecting surface concave in a plane transverse to the flow from said inner opening and merging with said upper surface at one end thereof, and
b. a second deflecting surface convex in a plane transverse to the flow from said inner opening and merging with said first deflecting surface at one end thereof and with said upper wall at said other end thereof.

24. An aerosol interface as in claim 23, wherein said upper wall defines the upper end of the aerosol interface.

25. An aerosol interface as in claim 20, wherein
a. said inner opening of said passageway has a height dimensioned by the spacing between said upper surface and said lower surface,
b. said channel opening defines a spacing extending between said upper wall and said lower wall at said terminal end,
c. said spacing of said channel opening being approximately twice the dimension as said spacing of said passageway inner opening,
d. said passageway having a width defined by said oppositely disposed end surfaces extending intermediate said upper and lower surfaces,
e. said width of said passageway being approximately twelve times greater than the dimension forming the height of said inner opening as defined by said upper and lower sufaces, and
f. said channel being of a length approximately ten times greater than the dimension forming said height spacing of said passageway inner opening.

26. An aerosol interface as in claim 25, wherein the cross-section formed by the spacing of said opening extending between said front and rear walls of said housing is in the range of approximately fifteen to twenty five times the cross-section defined by said spacing between said upper and lower surfaces of said passageway inner opening.

27. An aerosol interface as in claim 20, further including aerosol generating means coupled to said inlet means so as to provide a continuous supply of fluid to said chamber.

28. An aerosol interface as in claim 27, wherein said aerosol generating means includes a reservoir for containing a supply of liquid therein.

29. an aerosol interface as in claim 20, wherein said fluid stream attachment configuration comprises:
a. a first deflecting surface extending substantially in a vertical plane transverse to the flow from said inner opening and merging with said upper surface at one end thereof, and
b. a second deflecting surface extending substantially in a horizontal plane transverse to the flow from said inner opening and merging with said first deflecting surface at one end thereof and with said upper wall at said other end thereof.

30. An aerosol interface as in claim 20, wherein said channel opening extends below the elevation of said passageway inner opening with said control means extending therebetween.

31. An aerosol interface as in claim 30, wherein
a. said lower wall extends in substantially a vertical plane and said upper wall being outwardly inclined relative to said lower wall, and
b. said fluid stream attachment surface forming an arc extending in a plane transverse to the flow from said inner opening and merging with said upper surface at one end thereof and said upper wall at the opposite end thereof.

32. An aerosol interface as in claim 20, wherein said channel is characterized in that said upper wall and said lower wall have a cross-sectional area increasing in the flow direction from said channel opening to the atmosphere.

33. An aerosol interface as in claim 20, wherein
a. said breath transmission means is adapted to be positioned within the mouth of the user, and
b. said housing is adapted to be hand held by the user.

34. An aerosol interface as in claim 20, wherein said side walls of said channel coincide with the sidewalls of said housing.

35. An aerosol interface comprising:
A. a housing defining an aerosol fluid receiving chamber in open communication with the atmosphere at one end thereof,
B. inlet means operatively associated with said housing for permitting continuous delivery to said chamber of a flow of the aerosol fluid so as to obtain an accumulation of the aerosol fluid therein for inhalation by a patient using the aerosol during each inhalation period,
C. breath transmission means operatively associated with said housing on one side thereof for inhalation and exhalation by a patient, said transmission means comprising a passageway therethrough being defined by an inner opening at one end thereof and an outer opening at the other end thereof, said passageway being in direct continuously open fluidic communication with said chamber and extending above said inlet means,
D. said other end of said breath transmission means including said outer opening being adapted to be retained between the lips of the patient using the aerosol interface for the inhalation through said passageway of the aerosol fluid in said chamber and the exhalation of expired fluid by the patient into said passageway, E. outlet means operatively associated with said housing and displaced from said transmission means, said outlet means comprising a channel in direct fluidic communication with said chamber and with the atmosphere to permit a flow path for the expired fluid from the patient to exhaust to the atmosphere, and F. flow control means for fluidically coupling said transmission means and said outlet means, said control means directing substantially all of the expired fluid from said passageway inner opening to flow to the atmosphere through said channel of said outlet means without flowing into said chamber or forcing more than a minimal amount of the aerosol fluid contained in said chamber out through said outlet means during each patient exhalation period so as to maintain the aerosol fluid in said chamber substantially free of the expired fluid such that the aerosol fluid inspired by the patient during each inhalation period is primarily aerosol fluid from said chamber.

36. An aerosol interface as in claim 35, wherein said transmission means and said outlet means are situated on opposite sides of said housing.

37. An aerosol interface as in claim 35, wherein said transmission means and said outlet means are situated on the same side of said housing.

38. An aerosol interface as in claim 35, wherein a. said control means comprises a contoured fluid stream surface tending to direct the expired fluid breath flowing from said passageway inner opening directly toward said channel along said fluid stream surface as so to be conducive to a wall-hugging effect in the expired fluid as it passes through said chamber and into said channel such that it exits to the atmosphere, b. said channel is defined by an upper wall and a lower wall in spaced relationship to each other and a pair of oppositely disposed side walls extending intermediate said upper and lower walls, c. said upper wall merging at one end thereof with said contoured surface of said control means, d. said lower wall having a terminal end within said chamber, said spacing between said upper wall and said lower wall at said terminal end defining a channel opening to receive the expired fluid breath from said transmission means, e. said fluid stream surface includes
   (1) a first deflecting surface concave in a plane transverse to the flow from said inner opening and merging with said upper surface at one end thereof, and
   (2) a second deflecting surface convex in a plane transverse to the flow from said inner opening and merging with said first deflecting surface at one end thereof and with said upper wall at said other end thereof.

39. An aerosol interface as in claim 38, wherein said channel opening extends above the elevation of said passageway inner opening with said control means extending therebetween.

40. An aerosol interface as in claim 38, wherein said lower wall extends transversely across said chamber at one end thereof to provide a spacing between said terminal end and said inner opening of said passageway so as to obtain a flow path for the aerosol fluid to gain entry to said passageway from said chamber.

41. An aerosol interface adapted to be used by a human patient comprising:

A. an elongated hollow housing adapted to be held substantially vertically by a patient when in use and having an upper end opening and a lower end opening continuously open to the atmosphere, B. an opening in said housing intermediate its ends for enabling an aerosol fluid to be introduced into the interior of said housing, C. mouthpiece means adapted to be received into the mouth of a patient, said mouthpiece means being coupled to said housing adjacent its upper end opening and providing a direct, continuously open, passageway to and from a region adjacent said upper end opening for conveying inhaled and expired fluid between the mouth of the patient and the upper end opening region of said housing, D. outlet means spaced from said passageway and providing a direct, continuously open, channel between said upper end opening region and the surrounding atmosphere for conveying the expired fluid of the patient from the upper end opening region of said housing to the atmosphere, and E. flow control means interconnecting said mouthpiece passageway and said outlet means channel for directing substantially all of the expired fluid of the patient from said mouthpiece passageway through said outlet means channel to the atmosphere without entering the upper end opening of said housing.

42. In an aerosol administering system in which an aerosol generator supplies an aerosol fluid to an interface for enabling the aerosol fluid to be inhaled by a patient without substantial dilution by surrounding atmosphere or expired breath of the patient, an interface comprising:

A. a housing defining a chamber having opening means for direct and continuously open fluidic communication between the interior of the chamber and the atmosphere, B. inlet means adapted to receive aerosol fluid continuously from said generator into said chamber, C. first breath means in direct, continuously open fluidic communication with said chamber and having an opening for inhalation and exhalation by a patient, said opening means and said first breath means being remote from each other and said inlet means being located between them said first breath means defining a first breath flow path from said chamber to said opening for enabling aerosol fluid in the chamber to flow to the patient upon inhalation, and D. second breath means in direct, continuously open fluidic communication with the opening of said first breath means and the atmosphere, said second breath means defining a second breath flow path extending from the opening of said first breath means to the atmosphere, said second breath means including a fluid stream attachment surface for directing substantially all of an expired breath along said surface from the opening to the atmosphere.

43. The system of claim 42 wherein said housing opening means is at one end of the chamber and said first breath means is at another end so as to provide substantially only aerosol fluid from said chamber to the opening of said first means during at least a portion of a patient's inhalation period.

* * * * *

UNITED STATES PATENT OFFICE
CERTIFICATE OF CORRECTION

Patent No. 4,173,977    Dated Nov. 13, 1979

Inventor(s) Henry L. Burns

It is certified that error appears in the above-identified patent and that said Letters Patent are hereby corrected as shown below:

Col. 3, last line, after "opening" insert -- . The second deflecting surface interconnects--. Col. 4, lines 1 and 2, "the first deflecting surface at one end thereof" should read --the other end of the first deflecting surface--; line 28, "novle" should read --novel--. Col. 9, line 25, "searate" should read --separate--. Col. 13, line 39, after "diverge" insert --to--. Col. 16, line 11, "an" should read --An--. Col. 17, line 8, after "direct" insert --continuously open--.

Signed and Sealed this

Twelfth Day of February 1980

[SEAL]

Attest:

SIDNEY A. DIAMOND

Attesting Officer

Commissioner of Patents and Trademarks